United States Patent

Jonec

[11] Patent Number: 5,566,400
[45] Date of Patent: Oct. 22, 1996

[54] FLAT-FOLDED DISPOSABLE MALE URINARY AID AND COMPACT PORTABLE DISPENSER THEREFOR

[76] Inventor: Viliam Jonec, 19015 Rosita St., Tarzana, Calif. 91356

[21] Appl. No.: 216,906

[22] Filed: Mar. 22, 1994

[51] Int. Cl.$^6$ ................................ A47K 11/12
[52] U.S. Cl. ................ 4/144.4; 4/144.2; 4/144.3
[58] Field of Search ................ 4/144.1, 144.2, 4/144.3, 144.4, 114.1, DIG. 5; 604/326, 329, 349; 428/43, 34.1, 34.2, 34.3, 36.9, 36.91, 906; 239/93, 4.5; 141/337, 339, 331

[56] References Cited

U.S. PATENT DOCUMENTS

| | | | |
|---|---|---|---|
| 75,658 | 3/1868 | Van Rennsselaer | 4/144.3 |
| 2,878,486 | 3/1959 | Bartlett et al. | 4/144.4 |
| 3,200,415 | 8/1965 | Breece, Jr. | 4/144.2 |
| 3,295,145 | 1/1967 | Ericson | 4/144.3 |
| 3,591,870 | 7/1971 | Friesen et al. | 4/144.2 |
| 3,976,026 | 8/1976 | Beach | 4/144.1 |
| 4,023,216 | 5/1977 | Li | 4/144.1 |
| 4,296,502 | 10/1981 | Bortle | 4/144.1 |
| 4,608,046 | 8/1986 | Towfigh | 4/144.3 |
| 4,734,941 | 4/1988 | Dewitt et al. | 4/144.2 |
| 4,937,890 | 7/1990 | Tafur | 4/144.1 |
| 5,065,459 | 11/1991 | Tjahaja et al. | 4/144.2 |
| 5,243,712 | 9/1993 | Cross | 4/144.4 |
| 5,300,052 | 4/1994 | Kubo | 4/144.3 |

FOREIGN PATENT DOCUMENTS

| | | | |
|---|---|---|---|
| 555607 | 8/1993 | European Pat. Off. | 4/144.2 |
| 2508975 | 9/1976 | Germany | 4/144.2 |

*Primary Examiner*—Henry J. Recla
*Assistant Examiner*—Charles R. Eloshway
*Attorney, Agent, or Firm*—John J. Posta, Jr.

[57] ABSTRACT

A disposable male urinary aid which allows a man to urinate directly into a toilet from a standing position by channeling the urine directly into water contained in the toilet bowl. The urinary aid is made of temporarily waterproof paper, and is tapered from a larger diameter at the top end thereof, to a smaller diameter at the bottom end thereof. Following use, the urinary aid may be flushed down the toilet, since it is made entirely of biodegradeable materials. A dispenser is provided to hold and dispense a plurality of the urinary aids, which are stored in the dispensed in a folded, non-interleaved fashion.

3 Claims, 2 Drawing Sheets

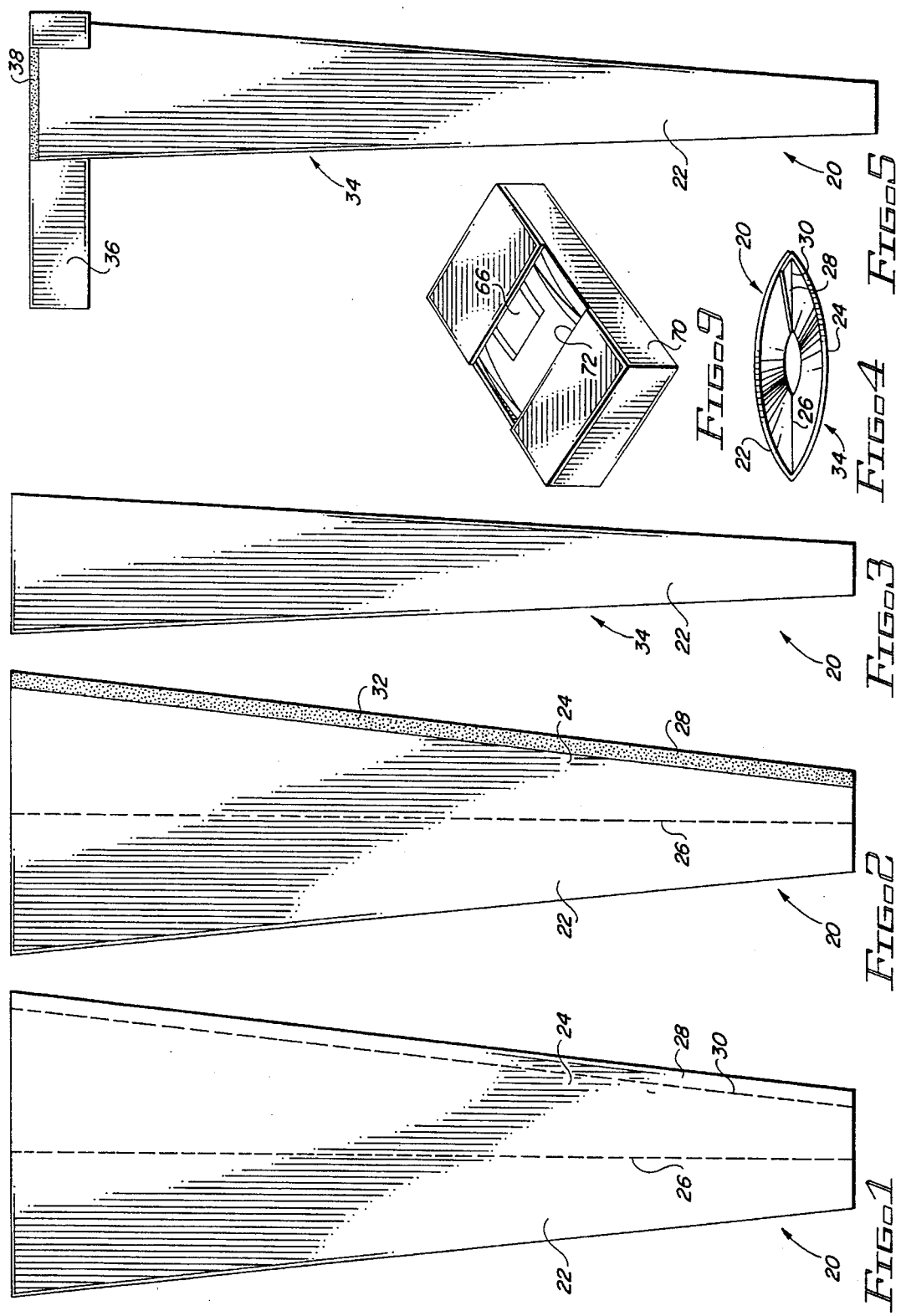

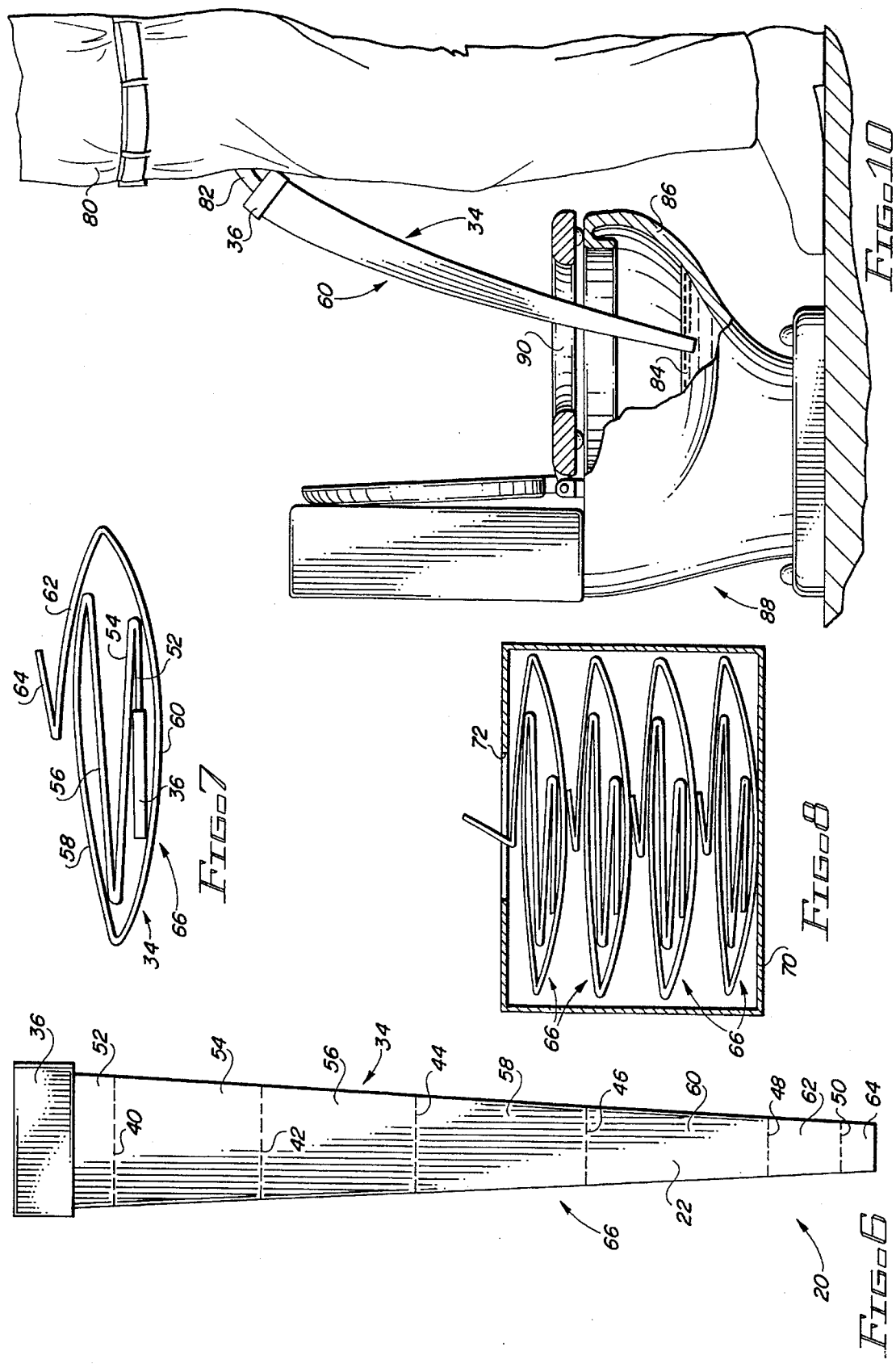

FLAT-FOLDED DISPOSABLE MALE URINARY AID AND COMPACT PORTABLE DISPENSER THEREFOR

BACKGROUND OF THE INVENTION

FIELD OF THE INVENTION

The present invention relates generally to the field of male hygienic devices, and more particularly to a convenient, disposable male urinary aid which allows a man to urinate directly into a toilet from a standing position by channeling the urine directly into water contained in the toilet.

During the course of a normal day, most people will leave the comfort of their homes for a variety of reasons ranging from work, to shopping, to social events, and so forth. Such travel away from the home can range from a matter of hours to extended out-of-town trips which can last from days to weeks. With few exceptions, people will invariably find it necessary on a daily basis (or several times daily) to use toilet facilities which are outside their homes.

While toilet facilities exist in nearly every conceivable location in which people are likely to travel, the cleanliness of such facilities varies considerably. While some toilet facilities are maintained in spotless condition, others may be poorly or infrequently maintained, and may be filthy at best. Even the best of public facilities will quickly become unsanitary when used by individuals lacking proper toilet manners. Unfortunately, at times there simply is no choice but to use such unsanitary toilet facilities despite their unsanitary condition.

Women have been concerned about this problem for a long time, particularly since their anatomy makes it rather difficult to urinate from a standing position. The art has recognized this problem and has devised various solutions, including those taught in U.S. Pat. No. 2,690,658, to Willis; U.S. Pat. No. 4,023,216, to Li; U.S. Pat. No. 4,937,890, to Tafur; and U.S. Pat. No. 5,091,998, to Irazabal. The Li device and the Irazabal device are both rigid and are generally unsuitable for use outside of the home. However, the Willis device and the Tafur device are compact and disposable, and accordingly represent a solution accommodating the female anatomy to represent potential solutions to this problem for women.

Since men are able to urinate from a standing position, the problem is less severe for them than it is for women, particularly when using toilet facilities having urinals. When only a toilet is available, however, the same problem of unsanitary conditions also faces men, although to a lesser degree. While men can urinate into a toilet from a standing position, they are faced with the option of either lifting the toilet seat first, or engaging in socially unacceptable behavior and possibly urinating at least in part on the toilet seat. The toilet seat may be unsanitary and may carry germs, and thus lifting the seat may be unappealing, particularly if the last user did not lift the seat before urinating.

Another problem is that some men are uncomfortable with the noise generated by urinating into a toilet from a standing position, particularly when they are in a public toilet with others, rather than in a private toilet. In some cases, this difficulty can cause an inability to urinate until others have left the toilet. In addition, some men have difficulty aiming accurately—and are thus left with the choice of either cleaning up the toilet after urinating, or of leaving the toilet in a soiled condition.

The art has presented three potential solutions for men, all of which have accompanying problems of their own. These solutions are a modified toilet device having a urinal attachment, a wearable urinary appliance for storing urine which may be worn on the body, and a portable urinal. Examples of these three types of devices illustrate the fact that they do not represent a solution to the problems being discussed herein.

The first type of device is used to convert a conventional toilet into a urinal, and is illustrated by U.S. Pat. No. 3,412,408, to Michal, Jr.; U.S. Pat. No. 3,500,480, also to Michal, Jr.; U.S. Pat. No. 3,822,419, to Wilson, Sr.; and U.S. Pat. No. 4,985,940, to Jones. These devices are all more or less permanently attached to a toilet, and thus are certainly not portable. In addition, even if they were attached to a public toilet, most men would not use them due to the fact that their designs make them inherently unlikely to remain sanitary in a public toilet facility.

The second type of device is the wearable urinary appliance, and is illustrated by U.S. Pat. No. 1,490,793, to Ajamian, et al.; U.S. Pat. No. 2,840,079, to Conway et al.; U.S. Pat. No. 3,032,038, to Swinn; U.S. Pat. No. 3,306,296, to Moss et al.; U.S. Pat. No. 3,358,538, to Carrigan; U.S. Pat. No. 3,559,651, to Moss; U.S. Pat. No. 4,820,291, to Terauchi, et al.; and U.S. Pat. No. 4,846,816, to Manfredi. These devices all require the user to urinate into a container strapped to the body or a limb of the body and worn, and are more appropriate for incontinent men than for men who are not incontinent but rather merely faced with concerns about the sanitation of public toilet facilities.

The third type of device is a portable urinal, and is illustrated by U.S. Pat. No. 2,699,781, to Koch; U.S. Pat. No. 3,164,186, to Weber et al.; U.S. Pat. No. 3,403,410, to Benzel et al.; U.S. Pat. No. 3,432,865, to Schwartz; U.S. Pat. No. 4,294,582, to Naslund; and U.S. Pat. No. 5,235,705, to Belisle. These devices are simply not convenient, since they are not small enough to be carried (comfortably) by a man in his pocket, and since they present a disposal problem which is a greater problem than all of the aforementioned problems encountered when using public toilets.

It is accordingly the primary objective of the present invention that it present an improved urinary aid for facilitating urination by men from a standing position into a toilet. It is a related objective that the urinary aid of the present invention must act as a conduit for urine leading directly from the man's penis into the water of the toilet bowl to preclude a misdirected stream of urine, thereby ensuring both quiet urination and that the toilet seat will remain clean even when in its lowered position. It is an additional objective that the urinary aid of the present invention fit directly onto the penis, thereby compensating for those men who have difficulty in aiming accurately and directing urine into the water in the toilet bowl in an accurate manner.

It is a further objective of the urinary aid of the present invention that it be convenient to use, and that it may be easily and quickly deployable without requiring undue effort. As such, it is an objective of the urinary aid of the present invention that it be temporarily waterproof while in use, but that it be disposable (and biodegradable) by dropping it into the toilet and flushing it following its use. It is yet an additional objective of the urinary aid of the present invention that it be compact in size, and that it be foldable to a small, flat configuration which may be carried in a pocket.

An additional objective of the present invention is the provision of a portable dispenser for use in dispensing a plurality of individual ones of the urinary aid. As such, the dispenser for the urinary aid of the present invention must be of construction which is relatively durable, and it must remain so for an extended period of time when carried in the pocket of the user to prevent degradation of the urinary aids carried inside the dispenser.

In order to enhance the market appeal of the urinary aid of the present invention, it should be of inexpensive manufacture to thereby afford it the broadest possible market. Finally, it is also an objective that all of the aforesaid advantages and objectives of the urinary aid of the present invention be achieved without incurring any substantial relative disadvantage.

SUMMARY OF THE INVENTION

The disadvantages and limitations of the background art discussed above are overcome by the present invention. With this invention, a disposable urinary aid made of temporarily waterproof paper is provided to channel urine from the penis of a man into the water located in a toilet bowl. The urinary aid is tapered from a larger diameter at the top end thereof, to a smaller diameter at the bottom end thereof. A dispenser may be provided to hold and dispense a plurality of the urinary aids, which are stored in the dispenser in a folded, non-interleaved fashion.

The urinary aid is made of thin, lightweight paper which is coated to be at least temporarily waterproof, yet which is sufficiently biodegradeable to allow it to be flushed to dispose of the urinary aid once it is used. The waterproof paper is folded to form a tapered structure, with the open sides of the urinary aid being adhesively secured together. The top end of the urinary aid, which is of a larger diameter, and the bottom end of the urinary aid, which is of a smaller diameter, are open to allow liquid into and out of the urinary aid, respectively.

In the preferred embodiment, a segment of soft, absorbent tissue is adhesively secured adjacent the top end of the urinary aid to allow the user to dry off his penis after using the urinary aid. The urinary aid is flat when formed, and may be folded into a compact configuration with the bottom end tending to spring up. A plurality of the folded urinary aids may be stored in a portable dispenser in a non-interleaved fashion, with the bottom end of the urinary aids located in an orientation such that they tend to spring up through a slot located in the top side of the portable dispenser. The portable dispenser may be made of thin, flexible plastic material so that it may be easily and conveniently carried on the person of the user.

In operation, the urinary aid on the top inside the portable dispenser will have its bottom end extending through the slot in the portable dispenser. By pulling the bottom end of the urinary aid, the entire urinary aid may be removed from the dispenser. Since the urinary aids are not interleaved within the portable dispenser, only one urinary aid will be removed from the portable dispenser at a time.

The larger top end of the urinary aid is placed snugly over the end of the user's penis, and the smaller bottom end of the urinary aid is placed into the water in a toilet bowl. When so placed, the water in the toilet bowl will tend to retain the bottom end of the urinary aid therein. The user may then urinate, and the urine will be funneled through the interior of the urinary aid, and into the toilet. When the user is done, he may remove the top end of the urinary aid from his penis, and use the soft tissue on the outside of the urinary aid to wipe his penis off. He may then drop the urinary aid into the toilet, and flush it away.

It may therefore be seen that the present invention teaches an improved urinary aid for facilitating the urination by men from a standing position into a toilet. The urinary aid of the present invention acts as a conduit for urine from the man's penis into the water of the toilet bowl to preclude a misdirected stream of urine, thereby ensuring both quiet urination and that the toilet will remain clean even when in its lowered position. The urinary aid of the present invention fits directly onto the penis, and thereby compensates for those men who otherwise have difficulty in aiming accurately and directing urine into the water in the toilet bowl in an accurate manner.

The urinary aid of the present invention is convenient to use, and it is easily and quickly deployable without requiring undue effort. The urinary aid of the present invention is temporarily waterproof while in use, but is disposable (and biodegradeable) and may be dropped into the toilet and flushed following its use. The urinary aid of the present invention is compact in size, and is foldable to a small, flat configuration which may be conveniently carried in a pocket.

The urinary aid of the present invention may be dispensed individually from a portable dispenser containing a plurality of individual ones of the urinary aid. The dispenser for the urinary aid of the present invention is quite durable, and will remain so for an extended period of time when carried in the pocket of the user, thereby preventing degradation of the urinary aids carried inside the dispenser.

The urinary aid of the present invention is of inexpensive manufacture, thereby making it eminently affordable and providing it with the broadest possible market. Finally, all of the aforesaid advantages and objectives of the urinary aid of the present invention are achieved without incurring any substantial relative disadvantage.

DESCRIPTION OF THE DRAWINGS

These and other advantages of the present invention are best understood with reference to the drawings, in which:

FIG. 1 is a top plan view of a segment of waterproof paper for use in making the urinary aid of the present invention, showing a first longitudinal fold line separating the waterproof paper into a first half and a second half, and a second longitudinal fold line separating the second half of the halves of the waterproof paper from a flap;

FIG. 2 is a top plan view of the waterproof paper illustrated in FIG. 1, showing the flap folded over onto the second half along the second longitudinal line, and also showing adhesive located on the outer side of the flap;

FIG. 3 is a top plan view of the waterproof paper illustrated in FIGS. 1 and 2, showing the first half of the waterproof paper folder folded over onto the second half along the first longitudinal line and into contact with the side of the flap (not shown in FIG. 3) on which the adhesive is located to form the urinary aid of the present invention;

FIG. 4 is an end view of the urinary aid illustrated in FIG. 3 from the top end thereof, showing the interior thereof;

FIG. 5 is a top plan view of the urinary aid as illustrated in FIG. 3, with a segment of tissue adhesively secured to the back side of the urinary aid near the top edge thereof by adhesive, with the segment of tissue extending out to the left side of the urinary aid, and also showing adhesive located on the front side of the urinary aid near the top edge thereof;

FIG. 6 is a top plan view of the urinary aid as illustrated in FIG. 5, with the segment of tissue secured to the front side of the urinary aid, and also showing a plurality of laterally extending fold lines along which the urinary aid will be folded for storage;

FIG. 7 is an edge view of the urinary aid of FIG. 6 folded along its fold lines, showing the bottom end of the urinary aid extending from the top side of the folded urinary aid;

FIG. 8 is a schematic side view of a plurality of folded urinary aids similar to the one illustrated in FIG. 7 which are stored in a portable dispenser having a wide slot disposed in the top side thereof, with the urinary aids being stored in the portable dispenser in a non-interleaved manner;

FIG. 9 is a perspective view of the portable dispenser illustrated in FIG. 8, with the end of a single folded urinary aid extending from the slot of the portable dispenser; and FIG. 10 is a somewhat schematic view of a man using the urinary aid of the present invention to urinate from a standing position into a toilet, showing the top end of the urinary aid fitted snugly over the man's penis, and the bottom end of the urinary aid located in water contained in the bowl of the toilet.

DETAILED DESCRIPTION OF THE PREFERRED EMBODIMENT

The preferred embodiment of the present invention uses a thin material which is temporarily waterproof, but which is ultimately biodegradable when flushed down a toilet. One such material is coated paper, wherein the coating is water impermeable for at least a short period of time, but which will ultimately dissolve in water over a longer period of time. Thus, a thin grade of paper may be coated with this material to make it temporarily water impermeable, yet ultimately biodegradable when flushed. In the preferred embodiment, the paper used is similar in weight to a tissue paper material, and it is coated with this material. Throughout the balance of this description of the present invention, this coated paper material will be referred to as waterproof paper.

Referring first to FIG. 1, a segment of waterproof paper 20 is illustrated which is considerably longer than it is wide, and which is wider at the top thereof (as shown in FIG. 1) than it is at the bottom thereof (as shown in FIG. 1). For ease of construction, the sides and the top and bottom edges of the segment of waterproof paper 20 are all flat. The segment of waterproof paper 20 is divided into a first half 22 and a second half 24 by a first longitudinal line 26, with the first half 22 being shown on the left side of the first longitudinal line 26 in FIG. 1, and the second half 24 being shown in the right side of the first longitudinal line 26 in FIG. 1.

Located on the right side of the second half 24 in the segment of waterproof paper 20 is a flap 28, which is separated from the second half 24 by a second longitudinal line 30. The size of the first half 22 is identical to the size of the second half 24. The width of the flap 28 is small compared to the widths of the first half 22 and the second half 24.

Referring now to FIG. 2, the flap 28 is folded along the second longitudinal line 30 (FIG. 1) over onto the second half 24 as shown. Following this folding operation, adhesive material 32 is placed along the outer surface of the flap 28, which faces away from the second half 24. The adhesive material 32 is preferably a material which will be at least temporarily waterproof, but which will ultimately dissolve in water when flushed. The adhesive material 32 may be the same as the material used in coating the segment of waterproof paper 20 to make it temporarily waterproof.

Referring next to FIG. 3, the first half 22 is folded along the first longitudinal line 26 (FIG. 2) over onto the second half 24 (FIG. 2) as shown. In this folding operation, the side edge of the first half 22 opposite the first longitudinal line 26 will be placed over the second longitudinal line 30 (FIG. 1). In so doing, the portion of the first half 22 adjacent the side of the first half 22 opposite the first longitudinal line 26 will be secured to the flap 28 (FIG. 2) by the adhesive material 32 (FIG. 2). The resulting structure is a frustroconical segment 34 which is folded flat.

Referring now to FIG. 4, the interior of the frustroconical segment 34 is illustrated from the top end thereof. It will be appreciated by those skilled in the art that the frustroconical segment 34 will act as a fluid conduit or a funnel, such that fluid admitted into the top of the frustroconical segment 34 will pass therethrough to the bottom of the frustroconical segment 34. In practice, the length of the frustroconical segment 34 ranges between 20 and 36 inches, with approximately 27 inches being the preferred length. Similarly, in the preferred embodiment, when folded flat, the width of the frustroconical segment 34 is approximately four inches at the top end and one and three-eighths inches at the bottom end.

Referring next to FIG. 5, a segment of tissue 36 is illustrated located near the top end of the frustroconical segment 34. The segment of tissue is both soft and absorbent, and is essentially rectangular in shape. A thin bead of adhesive material 38 is located near the top edge of the frustroconical segment 34 on the outer surface thereof, and the segment of tissue 36 is thereby secured to the outer surface of the frustroconical segment 34 near the top end thereof.

In FIG. 5, the segment of tissue 36 is shown in the process of being wrapped around the frustroconical segment 34 to secure it in place using the adhesive material 38. The adhesive material 38 may be the same as the adhesive material 32. Referring to FIG. 6, the segment of tissue 36 is shown completely wrapped around the frustroconical segment 34 near the top end thereof. The segment of tissue 36 will function as a drying towel when the urinary aid of the present invention is used.

Note that in FIG. 6 the frustroconical segment 34 is divided into seven segments by six laterally extending fold lines 40, 42, 44, 46, 48, and 50. The fold line 40 is located between a first segment 52 and a second segment 54, the fold line 42 is located between the second segment 54 and a third segment 56, the fold line 44 is located between the third segment 56 and a fourth segment 58. The fold line 46 is located between the fourth segment 58 and a fifth segment 60, the fold line 48 is located between the fifth segment 60 and a sixth segment 62, and the fold line 50 is located between the sixth segment 62 and a seventh segment 64.

The frustroconical segment 34 with the segment of tissue 36 attached thereto is referred to as a urinary aid 66, which comprises the preferred embodiment of the present invention. The urinary aid 66 may be folded along the fold lines 40, 42, 44, 46, 48, and 50 for compact storage. The first segment 52, the second segment 54, the third segment 56, and the fourth segment 58 are folded in accordion-like fashion in alternating directions. The fifth segment 60 is folded around over the first segment 52, and the sixth segment 62 is folded around over the fourth segment 58. The seventh segment 64 is folded back onto the sixth segment 62, and, when not restrained, tends to spring upwardly as shown.

The urinary aid 66 is shown in FIG. 7 in slightly expanded form such that the detail of the various segments 52, 54, 56, 68, 60, 62, and 64 may be separable from each other. In actual storage, the various segments 52, 54, 56, 68, 60, 62, and 64 would lies close adjacent each other so that the urinary aid 66 is quite compact in its folded form.

Referring next to FIG. 8, a plurality of the folded urinary aids 66 are schematically illustrated stored within a portable dispenser 70. Note that disposed in the top side of the portable dispenser 70 is a wide slot 72 through which the urinary aids 66 may be removed. In the preferred embodiment, the portable dispenser 70 is made of thin, flexible plastic material. Note that due to the seventh segment 64 (FIG. 7) being folded back over the sixth segment 62 (FIG. 7), the seventh segment 64 tends to spring upwardly and through the wide slot 72.

In the view illustrated in FIG. 8, the portable dispenser 70 is shown as being relatively thick for clarity, when, in fact, it is rather thin. Referring to FIG. 9, the portable dispenser 70 is shown in perspective much as it is in the preferred embodiment—thin and flexible. In the preferred embodiment, the portable dispenser 70 is less than an inch thick.

Referring finally to FIG. 10, the urinary aid 66 is shown in use. A man 80 places the top end of the urinary aid 66 over his penis 82. The bottom end of the urinary aid 66 is placed into water 84 in a bowl 86 of a toilet 88. Note that the seat 90 is in its lowered position. The urinary aid 66 fits through the seat 90 into the bowl 86 of the toilet 88, where the bottom end of the urinary aid 66 rests in the water 84. The man 80 urinates, with the urine flowing through the urinary aid 66 and into the water 84 in the bowl 86 of the toilet 88.

During urination, there is virtually no sound, since the urine flows down the urinary aid 66 and into the water 84 rather than splashing down into the water 84. Note also that the seat 90 of the toilet 88 does not get wet during urination. When the man 80 is done urinating, he removes the top end of the urinary aid 66 from his penis 82. If the man 80 so desires, he may wipe off his penis 82 with the segment of tissue 36 located near the top end of the urinary aid 66. The man 80 then drops the urinary aid 66 through the seat 90 of the toilet 88 into the water 84, and flushes the toilet 88.

It may therefore be appreciated from the above detailed description of the preferred embodiment of the present invention that it teaches an improved urinary aid for facilitating the urination by men from a standing position into a toilet. The urinary aid of the present invention acts as a conduit for urine from the man's penis into the water of the toilet bowl to preclude a misdirected stream of urine, thereby ensuring both quiet urination and that the toilet will remain clean even when in its lowered position. The urinary aid of the present invention fits directly onto the penis, and thereby compensates for those men who otherwise have difficulty in aiming accurately and directing urine into the water in the toilet bowl in an accurate manner.

The urinary aid of the present invention is convenient to use, and it is easily and quickly deployable without requiring undue effort. The urinary aid of the present invention is temporarily waterproof while in use, but is disposable (and biodegradeable) and may be dropped into the toilet and flushed following its use. The urinary aid of the present invention is compact in size, and is foldable to a small, flat configuration which may be conveniently carried in a pocket.

The urinary aid of the present invention may be dispensed individually from a portable dispenser containing a plurality of individual ones of the urinary aid. The dispenser for the urinary aid of the present invention is quite durable, and will remain so for an extended period of time when carried in the pocket of the user, thereby preventing degradation of the urinary aids carried inside the dispenser.

The urinary aid of the present invention is of inexpensive manufacture, thereby making it eminently affordable and providing it with the broadest possible market. Finally, all of the aforesaid advantages and objectives of the urinary aid of the present invention are achieved without incurring any substantial relative disadvantage.

Although an exemplary embodiment of the present invention has been shown and described with reference to particular embodiments and applications thereof, it will be apparent to those having ordinary skill in the art that a number of changes, modifications, or alterations to the invention as described herein may be made, none of which depart from the spirit or scope of the present invention. All such changes, modifications, and alterations should therefore be seen as being within the scope of the present invention.

What is claimed is:

1. A method for preventing splashing of urine onto a toilet containing toilet water or about a toilet area by a male standing before the toilet and urinating into the toilet, comprising the steps of:

a) providing a flexible, bio-degradable, elongated tubular element having an inlet and an outlet end, b) inserting the penis into the inlet end of said element, c) disposing the outlet end into the toilet water, and d) urinating directly into the tubular element.

2. The method of claim 1 including the step of:

a) providing a segment of soft absorbent material secured to the tubular element, and b) drying the penis with said absorbent material after urinating.

3. The method of claim 2 and further including the step of placing the tubular element into the toilet water after using the tubular element.

* * * * *